(12) United States Patent
Toshimitsu et al.

(10) Patent No.: US 8,771,726 B2
(45) Date of Patent: Jul. 8, 2014

(54) NAIL PATCH

(75) Inventors: Arata Toshimitsu, Tsukuba (JP); Naoko Matsuda, Tsukuba (JP); Toshihiro Kogure, Tsukuba (JP); Kazuya Ishida, Tsukuba (JP)

(73) Assignee: Hisamitsu Pharmaceutical Co., Inc, Saga (JP)

( * ) Notice: Subject to any disclaimer, the term of this patent is extended or adjusted under 35 U.S.C. 154(b) by 1074 days.

(21) Appl. No.: 12/310,167

(22) PCT Filed: Jul. 6, 2007

(86) PCT No.: PCT/JP2007/063564
§ 371 (c)(1),
(2), (4) Date: Feb. 13, 2009

(87) PCT Pub. No.: WO2008/026381
PCT Pub. Date: Mar. 6, 2008

(65) Prior Publication Data
US 2009/0324696 A1    Dec. 31, 2009

(30) Foreign Application Priority Data
Aug. 28, 2006 (JP) ................ 2006-231126

(51) Int. Cl.
| A61F 13/02 | (2006.01) |
| A61F 13/00 | (2006.01) |
| A61K 31/135 | (2006.01) |
| A61K 9/00 | (2006.01) |
| A61K 31/137 | (2006.01) |
| A61K 47/26 | (2006.01) |
| A61K 47/12 | (2006.01) |
| A61K 47/14 | (2006.01) |
| A61K 47/32 | (2006.01) |

(52) U.S. Cl.
CPC ............... *A61K 31/137* (2013.01); *A61K 47/26* (2013.01); *A61K 9/0014* (2013.01); *A61K 47/12* (2013.01); *A61K 47/14* (2013.01); *A61K 47/32* (2013.01)
USPC ............................ 424/448; 424/449; 514/655

(58) Field of Classification Search
None
See application file for complete search history.

(56) References Cited

U.S. PATENT DOCUMENTS

| 5,212,199 A * | 5/1993 | Heiber et al. .......... 514/415 |
| 6,585,963 B1 | 7/2003 | Quan et al. |
| 6,727,401 B1 * | 4/2004 | Venkateshwaran et al. .... 602/41 |
| 2004/0142024 A1 | 7/2004 | Chono et al. |
| 2004/0265362 A1 | 12/2004 | Susilo |

FOREIGN PATENT DOCUMENTS

| EP | 1170004 A1 | 1/2002 |
| JP | 5-85929 | 4/1993 |
| JP | 9-504536 | 5/1997 |
| JP | 10-330247 | 12/1998 |
| JP | 2002-68975 | 3/2002 |
| JP | 2003-525641 | 9/2003 |
| JP | 2004-529923 | 9/2004 |
| JP | 205-501885 | 1/2005 |
| JP | 2005-41850 | 2/2005 |
| JP | 2005-041850 A | 2/2005 |
| JP | 2010-189440 A | 9/2010 |
| WO | WO-96/11710 | 4/1996 |
| WO | 9940955 A2 | 8/1999 |
| WO | 00/61120 A1 | 10/2000 |
| WO | 01/07018 A1 | 2/2001 |
| WO | 2005013955 A2 | 2/2005 |
| WO | 2005/115355 A1 | 12/2005 |

OTHER PUBLICATIONS

Uchida, K., et al., "Terbinafine no Keratin Shinwasei ni Kan suru Kento", *Japanese Journal of Medical Mycology*, vol. 34, No. 2, 1993, pp. 207-212.

Japan Pharmaceutical Excipients Council, Iyakuhin Tenkabutsu Jiten, 1994, p. 56.

Office Action issued on Mar. 29, 2011, in a counterpart Japanese patent application (No. P2008-531990), with English translation of cited documents; 3 pages total.

Notification of Information Provision issued on Mar. 22, 2011, in counterpart Japanese Patent Application No. 2008-531990.

* cited by examiner

*Primary Examiner* — Brian-Yong Kwon
*Assistant Examiner* — Jennifer A Berrios
(74) *Attorney, Agent, or Firm* — Nath, Goldberg & Meyer; Joshua B. Goldberg

(57) ABSTRACT

The present subject matter provides a nail patch comprising a backing layer and a pressure-sensitive adhesive layer disposed on at least one side of the backing layer, wherein the pressure-sensitive adhesive layer comprises a pressure-sensitive adhesive base, terbinafine and/or a pharmacologically acceptable salt thereof, and sodium acetate and/or sorbitan monolaurate as a solubilizer.

6 Claims, No Drawings

NAIL PATCH

TECHNICAL FIELD

The present invention relates to a nail patch, particularly, a nail patch comprising terbinafine as an antifungal agent.

BACKGROUND ART

Terbinafine has been known as an effective antifungal agent and used particularly in the treatment of tinea unguium. Tinea unguium is a difficult-to-treat disease that is caused by *Trichophyton* invasion into nails and characterized by symptoms such as opaque, thickened, and deformed nail surface. Tinea unguium is currently treated in most cases by means of the long-term oral administration of antifungal agents such as terbinafine or itraconazole. However, there are problems such as severe side effects such as liver damage, attributed to the long-term administration of the antifungal agents, and interaction with other agents.

By contrast, external preparations for nails, which have low drug permeation into blood, are thought to be able to reduce side effects attributed to the oral administration of antifungal agents. Some external preparations for nails comprising an antifungal agent have been proposed so far. However, these preparations do not provide the sufficient amount of the drug permeated into nails having high barrier functions. Therefore, they do not always have high therapeutic effects under present circumstances.

Such an external preparation for nails is, for example, a liquid medicine comprising an antifungal agent (Patent Document 1). However, for the liquid medicine, a dose to an affected part is difficult to adjust, and continued administration is also difficult. Therefore, it is thought that sufficient drug permeation into nails is not obtained. Moreover, a nail lacquer comprising an antifungal agent has also been proposed (Patent Document 2). This preparation permits continued administration. However, an administration method thereof is complicated. Additionally, it does not always have high drug permeability and, furthermore, might cause stained or discolored nails.

Furthermore, patches comprising an antifungal agent have also been proposed in terms of easy administration (Patent Documents 3 to 6). These nail patches provide more improved usability than those of external preparations other than patches, such as liquid medicines, and also permit long-lasting effects of the drug when directly attached to nails. Therefore, they have improved drug permeability into nails. However, the amount of the drug permeated sufficient for the treatment of tinea unguium still remains to be achieved.

Patent Document 1: Japanese Patent Laid-Open No. 2002-68975
Patent Document 2: Japanese Patent Laid-Open No. 5-85929
Patent Document 3: Japanese Patent Laid-Open No. 10-330247
Patent Document 4: National Publication of International Patent Application No. 2003-525641
Patent Document 5: National Publication of International Patent Application No. 1997-504536
Patent Document 6: National Publication of International Patent Application No. 2005-501885

DISCLOSURE OF THE INVENTION

Nails are skin appendages that are made of hard plates of keratinized epidermal cells over dorsal surfaces at the ends of fingers and toes and correspond to the stratum corneum in the skin. The stratum corneum of the skin is composed mainly of proteins with low sulfur contents, called soft keratins. By contrast, the nail is composed mainly of hard keratins with high sulfur contents and possesses properties as physico-chemically stable, poorly water-soluble proteins. Moreover, the nail has a much lower lipid content than that of the stratum corneum of the skin and therefore exhibits a behavior totally different from usual drug absorption into the skin.

Previous nail patches have high drug permeability into the skin due to improved drug permeability into nails and therefore deliver the antifungal drug into blood. As a result, they might cause the problem of side effects such as liver damage, as observed in oral administration.

The present invention has been achieved in consideration of the problems of the conventional nail patches by focusing on the difference of drug absorption behaviors between the nail and the skin. Specifically, an object of the present invention is to provide a nail patch that has sufficiently improved permeability of terbinafine, which is expected to be effective for tinea unguium, into nails, and permeability thereof into the skin reduced to an exceedingly low level.

The present inventors have completed the present invention by finding that a nail patch comprising sodium acetate and/or sorbitan monolaurate as a solubilizer is confirmed to have sufficient permeability of terbinafine and/or a pharmacologically acceptable salt thereof into nails, whereas it has exceedingly low permeability thereof into the skin.

Specifically, the present invention provides a nail patch comprising a backing layer and a pressure-sensitive adhesive layer disposed on at least one side of the backing layer, wherein the pressure-sensitive adhesive layer comprises a pressure-sensitive adhesive base, terbinafine and/or a pharmacologically acceptable salt thereof, and sodium acetate and/or sorbitan monolaurate as a solubilizer. Such a nail patch offers sufficient permeability into nails, whereas permeability into the skin can be reduced to an exceedingly low level. Moreover, the nail patch, which comprises the solubilizer, can comprise terbinafine and/or a pharmacologically acceptable salt thereof at a high content and can continuously deliver the drug at high doses into nails.

It is preferred that the pressure-sensitive adhesive base should comprise an acrylic pressure-sensitive adhesive. Moreover, it is preferred that the acrylic pressure-sensitive adhesive should be an acrylic copolymer having a hydroxyl or carboxylic acid group. The resulting nail patch can further enhance permeability into nails and can reduce permeability into the skin more effectively.

It is preferred that the pressure-sensitive adhesive layer should comprise 0.5 to 50% by mass of terbinafine and/or a pharmacologically acceptable salt thereof with respect to the whole mass of the layer. The concentration of 0.5 to 50% by mass is a higher concentration than that in a usual patch. Such a high concentration generally causes unfavorable phenomena such as reduced adhesive strength attributed to drug crystallization. However, the patch of the present invention can dissolve therein terbinafine at a high concentration and therefore, can continuously deliver the drug at high doses into nails without causing such phenomena.

It is preferred that the pharmacologically acceptable salt of terbinafine should be terbinafine hydrochloride. The terbinafine hydrochloride, for the nail patch of the present invention, is particularly excellent in permeability into nails and effective as an antifungal agent.

It is preferred that the pressure-sensitive adhesive layer should further comprises a plasticizer. The pressure-sensitive adhesive layer, which comprises the plasticizer, can possess more easily adjustable softness and improved adhesion.

The nail patch of the present invention can have sufficiently improved permeability of terbinafine, which is expected to be effective for tinea unguium, into nails, and permeability thereof into the skin reduced to an exceedingly low level. The application of the nail patch of the present invention to a nail disease such as tinea unguium can more highly improve therapeutic effects on the nail disease such as tinea unguium than before and can minimize side effects, such as liver damage, attributed to terbinafine.

BEST MODES FOR CARRYING OUT THE INVENTION

A nail patch of the present invention comprises at least a backing layer and a pressure-sensitive adhesive layer disposed on at least one side of the backing layer. Moreover, a release sheet that is released at the time of use of the patch may further be laminated on the pressure-sensitive adhesive layer.

The backing layer is not particularly limited and is preferably any of those having no influence on the release of terbinafine comprised at a relatively high content in the pressure-sensitive adhesive layer. Specifically, a film or sheet of polyethylene, polypropylene, polybutadiene, an ethylene-vinyl acetate copolymer, polyvinyl chloride, polyester, Nylon (registered trademark), polyurethane, or the like, a laminate thereof, a composite material thereof, and the like can be used. Among them, the polyethylene, ethylene-vinyl acetate copolymer, and polyester are preferably used from the viewpoint of a fit of the patch attached to nails and influence on drug release. Any of stretchable and non-stretchable backing layers can be used. The stretchable one is preferable from the viewpoint of adhesion.

The pressure-sensitive adhesive layer comprises at least a pressure-sensitive adhesive base, terbinafine or a pharmacologically acceptable salt thereof as a drug, sodium acetate and/or sorbitan monolaurate as a solubilizer, and so on. In this context, it is preferred that no volatile solvent should be used in the pressure-sensitive adhesive layer, from the viewpoint of not causing stained or discolored nails.

The pressure-sensitive adhesive layer comprises at least terbinafine and/or a pharmacologically acceptable salt thereof as the drug. The concentration of the drug is preferably 0.5 to 50% by mass, more preferably 2.5 to 50% by mass, with respect to the whole mass of the pressure-sensitive adhesive layer. This concentration is a higher concentration than that in a usual patch. Such a high concentration generally causes unfavorable phenomena such as reduced adhesive strength attributed to drug crystallization. However, the patch of the present invention can dissolve therein terbinafine at a high concentration and therefore, can continuously deliver the drug at high doses into nails without causing such phenomena. The drug comprised at a concentration exceeding 50% by mass tends to have bad influence on the physical properties of the preparation, whereas the drug comprised at a concentration lower than 0.5% by mass tends to fail to be delivered in an amount sufficient for exhibiting therapeutic effects.

Hydrochloride, sulfate, mesilate, citrate, fumarate, tartrate, maleate, acetate, or the like of terbinafine can be used as the pharmacologically acceptable salt of terbinafine without particularly limitations as long as the effects of the present invention are obtained. Terbinafine hydrochloride, which is in the hydrochloride form of terbinafine, is particularly preferably used.

Moreover, the pressure-sensitive adhesive layer may optionally comprise, as a drug component, for example, azole-based antifungal drugs such as bifonazole, clotrimazole, tioconazole, miconazole, econazole, isoconazole, sulconazole, oxiconazole, croconazole, ketoconazole, neticonazole, lanoconazole, omoconazole, itraconazole, and fluconazole, allylamine-based antifungal drugs such as naftifine, benzylamine-based antifungal drugs such as butenafine, morpholine-based antifungal drugs such as amorolfine, thiocarbamine-based antifungal drugs such as liranaftate, naphthiomate N, tolnaftate (naphthiomate T), and tolciclate, fatty acid-based antifungal drugs such as undecylenic acid, zinc undecylenate, and phenyl-11-iodo-10-undecynoate, salicylic acid-based antifungal drugs such as salicylic acid, antifungal antibiotics such as siccanin, trichomycin, pyrrolnitrin, nystatin, pimaricin, griseofulvin, and variotin, polyene-based antifungal drugs such as amphotericin B, benzamide-based antifungal drugs such as exalamide, pyrimidine-based antifungal drugs such as ciclopiroxolamine, iodopropargyl-based antifungal drugs such as haloprogin, zinc diethyldithiocarbamate, thianthol, flucytosine, 2,4,6-tribromophenyl caproate, trimethylcetylammonium pentachlorophenate, sulfur, and the bark of *Hibiscus syriacus*, or salts thereof.

Examples of a pressure-sensitive adhesive component in the pressure-sensitive adhesive base include acrylic, rubber-based, and silicone-based pressure-sensitive adhesives. Among them, the acrylic pressure-sensitive adhesive is preferably used.

The acrylic pressure-sensitive adhesive is not particularly limited as long as it is a polymer or copolymer comprising at least one (meth)acrylic acid derivative typified by 2-ethylhexyl acrylate, methyl acrylate, butyl acrylate, hydroxyethyl acrylate, 2-ethylhexyl methacrylate, or the like. For example, pressure-sensitive adhesives such as an acrylic acid-octyl acrylate copolymer, a 2-ethylhexyl acrylate-vinyl pyrrolidone copolymer solution, an acrylate-vinyl acetate copolymer, a 2-ethylhexyl acrylate-2-ethylhexyl methacrylate-dodecyl methacrylate copolymer, a methyl acrylate-2-ethylhexyl acrylate copolymer resin emulsion, and an acrylic polymer comprised in an alkanolamine solution of an acrylic resin, which are listed as pressure-sensitive adhesives in Japanese Pharmaceutical Excipients Directory 2005 (edited by Japan Pharmaceutical Excipients Council), EUDRAGIT series (Higuchi Inc.), and DURO-TAK acrylic pressure-sensitive adhesive series (manufactured by National Starch And Chemical Company) can be used. Among them, the pressure-sensitive adhesive, which is an acrylic copolymer having a hydroxyl or carboxylic acid group, can be used preferably from the viewpoint of adhesion to nails and drug release. In this context, the acrylic pressure-sensitive adhesive having a hydroxyl or carboxylic acid group refers to a copolymer of two or more (meth)acryloyl monomers (which refer to monomers comprising a (meth)acryloyl group)), which has a hydroxyl or carboxyl group or a copolymer of a (meth)acryloyl monomer and a monomer having an ethylenic unsaturated group (except for (meth)acryloyl monomers), which has a hydroxyl or carboxyl group and is a compound exhibiting adhesion. Among them, the DURO-TAK acrylic pressure-sensitive adhesive series are preferably used.

The acrylic pressure-sensitive adhesive may comprise a rubber component of the rubber-based pressure-sensitive adhesive. Such a rubber component can be exemplified by natural rubber, styrene-butadiene rubber, a styrene-isoprene-styrene block copolymer (SIS), a styrene-butadiene-styrene block copolymer, polyisobutylene (PIB), polyisoprene, and butyl rubber. Among them, at least one selected from the natural rubber, styrene-isoprene-styrene block copolymer, polyisobutylene, and polyisoprene is preferably used, from the viewpoint of easy quality design and cost.

The mass of the pressure-sensitive adhesive base is preferably 5 to 85% by mass, more preferably 10 to 80% by mass, with respect to the whole mass of the pressure-sensitive adhesive layer.

The pressure-sensitive adhesive layer may comprise a plasticizer. Examples of the plasticizer that can be used include: petroleum-based oils such as paraffin-based process oil, naphthene-based process oil, and aromatic process oil; squalane and squalene; plant oils such as olive oil, camellia oil, castor oil, tall oil, and peanut oil; silicon oil; dibasic acid esters such as dibutyl phthalate and dioctyl phthalate; liquid rubbers such as polybutene and liquid isoprene rubber; liquid fatty acid esters such as isopropyl myristate, hexyl laurate, diethyl sebacate, and diisopropyl sebacate; and diethylene glycol, polyethylene glycol, glycol salicylate, propylene glycol, dipropylene glycol, triacetin, triethyl citrate, and crotamiton. Particularly, liquid paraffin, liquid polybutene, isopropyl myristate, diethyl sebacate, and hexyl laurate are preferable.

The pressure-sensitive adhesive layer comprises sodium acetate and/or sorbitan monolaurate as the solubilizer. The pressure-sensitive adhesive layer, which comprises these solubilizers, enhances the permeability of the drug (particularly, terbinafine and/or pharmacologically acceptable salt thereof) into nails, whereas the permeability thereof into the skin is reduced to an exceedingly low level. Moreover, this effect becomes higher at a sodium acetate content of 0.5 to 30% by mass, preferably 1 to 20% by mass, with respect to the whole mass of the pressure-sensitive adhesive layer. For sorbitan monolaurate, its content is preferably 0.5 to 20% by mass, more preferably 1 to 10% by mass, with respect to the whole mass of the pressure-sensitive adhesive layer.

Moreover, the pressure-sensitive adhesive layer comprises the sodium acetate and the sorbitan monolaurate at a ratio of preferably 1:40 to 60:1. More preferably, the pressure-sensitive adhesive layer comprises the three components, i.e., "terbinafine and/or a pharmacologically acceptable salt thereof (e.g., terbinafine hydrochloride)", "sodium acetate", and "sorbitan monolaurate", at a ratio of 100:100:100 to 100:60:40 for enhancing absorption into nails. The pressure-sensitive adhesive layer comprising the three components at the ratio can sufficiently dissolve therein "terbinafine and/or a pharmacologically acceptable salt thereof" comprised even at a content of 0.5% by mass or more and further improves permeability into nails. By contrast, the pressure-sensitive adhesive layer comprising the three components at the ratio can reduce the permeability of the drug into the skin to an exceedingly low level. As a result, drug delivery into the systemic circulatory system can be prevented, resulting in more reduction in side effects. Furthermore, only permeability into nails can be improved, leading to sufficient drug delivery to infected sites. Thus, therapeutic effects can be exhibited efficiently.

The pressure-sensitive adhesive layer of the nail patch comprises a tackifier in addition to the agents described above and optionally comprises components such as absorption promoters, antioxidants, UV absorbers, pigments, cross-linking agents, fillers, and preservatives.

Examples of the tackifier include: rosin and rosin derivatives such as rosin glycerin ester, hydrogenated rosin, hydrogenated rosin glycerin ester, and rosin pentaerythritol ester; alicyclic saturated hydrocarbon resins such as ARKON P100 (Arakawa Chemical Industries, Ltd.); aliphatic hydrocarbon resins such as Quintone B170 (Zeon Corp.); terpene resins such as Clearon P-125 (Yasuhara Chemical Co., Ltd.); and maleic acid resins.

Examples of the absorption promoters optionally comprised therein include fatty acid, fatty alcohol, fatty acid esters, amides, or ethers, aromatic organic acids, aromatic alcohol, aromatic organic acid esters or ethers having 6 to 20 carbon atoms (all of which may be saturated or unsaturated and may be in a cyclic, linear, or branched form) and further include lactates, acetates, monoterpene compounds, sesquiterpene compounds, Azone, Azone derivatives, pirotiodecane, glycerin fatty acid esters, propylene glycol fatty acid esters, sorbitan fatty acid esters (Span type), polysorbate (Tween type), polyethylene glycol fatty acid esters, polyoxyethylene hydrogenated castor oil (HCO type), polyoxyethylene alkyl ethers, sucrose fatty acid esters, and plant oils.

Specifically, the absorption promoters are preferably caprylic acid, capric acid, caproic acid, lauric acid, myristic acid, palmitic acid, stearic acid, isostearic acid, oleic acid, linoleic acid, linolenic acid, lauryl alcohol, myristyl alcohol, oleyl alcohol, isostearyl alcohol, cetyl alcohol, methyl laurate, hexyl laurate, lauric acid diethanolamide, isopropyl myristate, myristyl myristate, octyldodecyl myristate, cetyl palmitate, salicylic acid, methyl salicylate, ethylene glycol salicylate, cinnamic acid, methyl cinnamate, cresol, cetyl lactate, lauryl lactate, ethyl acetate, propyl acetate, geraniol, thymol, eugenol, terpineol, 1-menthol, borneol, d-limonene, isoeugenol, isoborneol, nerol, dl-camphor, glycerin monocaprylate, glycerin monocaprate, glycerin monolaurate, glycerin monooleate, sorbitan monolaurate, sucrose monolaurate, polysorbate 20, propylene glycol, propylene glycol monolaurate, polyethylene glycol monolaurate, polyethylene glycol monostearate, polyoxyethylene lauryl ether, HCO-60, pirotiodecane, and olive oil, particularly preferably, lauryl alcohol, isostearyl alcohol, lauric acid diethanolamide, glycerin monocaprylate, glycerin monocaprate, glycerin monooleate, sorbitan monolaurate, propylene glycol monolaurate, polyoxyethylene lauryl ether, and pirotiodecane.

Examples of the antioxidants include tocopherol and ester derivatives thereof, ascorbic acid, ascorbyl stearate, nordihydroguaiaretic acid, dibutylhydroxytoluene (BHT), and butylhydroxyanisole.

The fillers are preferably calcium carbonate, magnesium carbonate, silicate (e.g., aluminum silicate and magnesium silicate), silicic acid, barium sulfate, calcium sulfate, calcium zincate, zinc oxide, titanium oxide, and the like.

The cross-linking agents are preferably thermosetting resins (e.g., amino resins, phenol resins, epoxy resins, alkyd resins, and unsaturated polyester), isocyanate compounds, block isocyanate compounds, organic cross-linking agents, and inorganic cross-linking agents (e.g., metals or metal compounds).

The preservatives are preferably ethyl parahydroxybenzoate, propyl parahydroxybenzoate, butyl parahydroxybenzoate, and the like.

The UV absorbers are preferably p-aminobenzoic acid derivatives, anthranilic acid derivatives, salicylic acid derivatives, coumarin derivatives, amino acid compounds, imidazoline derivatives, pyrimidine derivatives, dioxane derivatives, and the like.

The pressure-sensitive adhesive layer is protected with the release sheet, preferably before use of the nail patch, i.e., during storage thereof. The release sheet is released at the time of use of the patch.

The release sheet is not particularly limited. Polyethylene, polypropylene, or polyester subjected to release treatment is preferably used.

A method for producing the nail patch is not particularly limited as long as it is a method usually used. One example thereof includes a method comprising: thermally melting a drug-containing base composition; coating a release sheet or a backing layer with the solution; and bonding together the laminate and the backing layer or the release sheet. Alternatively, the present agent can be obtained by: dissolving a drug-containing base component in a solvent such as toluene, hexane, or ethyl acetate; extending the solution on a release sheet or a backing layer, followed by removal of the solvent by drying; and then bonding together the laminate and the backing layer or the release sheet.

EXAMPLES

Hereinafter, the present invention will be described more specifically with reference to Examples. However, the present invention is not intended to be limited to these Examples. Various changes or modifications can be made without departing from the technical principles of the present invention. In Examples, "%" means "% by mass".

Example 1

A nail patch comprising the composition shown in Table 1 below was produced. Specifically, terbinafine hydrochloride, sodium acetate, and isopropyl myristate were placed in a mortar in advance and well mixed. Then, this mixture was mixed with an acrylic pressure-sensitive adhesive dissolved in ethyl acetate. A release sheet was coated with the solution, followed by removal of the solvent ethyl acetate by drying. The laminate and a PET film backing layer were bonded together to obtain a nail patch of Example 1.

TABLE 1

| | |
|---|---|
| Terbinafine hydrochloride | 5.00% |
| Acrylic pressure-sensitive adhesive (DURO-TAK 87-2194, National Starch And Chemical Company) | 84.10% |
| Isopropyl myristate | 8.40% |
| Sodium acetate | 2.50% |
| Total | 100.00% |

Example 2

A nail patch of Example 2 was obtained in the same way as in Example 1 except that an acrylic pressure-sensitive adhesive (DURO-TAK 87-2516, National Starch And Chemical Company) was used instead of the acrylic pressure-sensitive adhesive (DURO-TAK 87-2194, National Starch And Chemical Company).

Example 3

A nail patch comprising the composition shown in Table 2 below was produced. Specifically, terbinafine hydrochloride, sodium acetate, sorbitan monolaurate, and isopropyl myristate were placed in a mortar in advance and well mixed. Then, this mixture was mixed with an acrylic pressure-sensitive adhesive dissolved in ethyl acetate. A release sheet was coated with the solution, followed by removal of the solvent ethyl acetate by drying. The laminate and a PET film backing layer were bonded together to obtain a nail patch of Example 3.

TABLE 2

| | |
|---|---|
| Terbinafine hydrochloride | 5.00% |
| Acrylic pressure-sensitive adhesive (DURO-TAK 87-2516, National Starch And Chemical Company) | 81.10% |
| Isopropyl myristate | 8.40% |
| Sodium acetate | 2.50% |
| Sorbitan monolaurate | 3.00% |
| Total | 100.00% |

Example 4

A nail patch of Example 4 was obtained in the same way as in Example 3 except that Tween 80 was used instead of the sorbitan monolaurate.

Comparative Example 1

A nail patch comprising the composition shown in Table 3 below was produced. Specifically, terbinafine hydrochloride and isopropyl myristate were placed in a mortar in advance and well mixed. Then, this mixture was mixed with an acrylic pressure-sensitive adhesive dissolved in ethyl acetate. A release sheet was coated with the solution, followed by removal of the solvent ethyl acetate by drying. The laminate and a PET film backing layer were bonded together to obtain a nail patch of Comparative Example 1.

TABLE 3

| | |
|---|---|
| Terbinafine hydrochloride | 5.00% |
| Acrylic pressure-sensitive adhesive (DURO-TAK 87-2516, National Starch And Chemical Company) | 86.40% |
| Isopropyl myristate | 8.60% |
| Total | 100.00% |

Example 5

A nail patch comprising the composition shown in Table 4 below was produced. Specifically, terbinafine hydrochloride, sodium acetate, sorbitan monolaurate, and isopropyl myristate were placed in a mortar in advance and well mixed. Then, this mixture was mixed with an acrylic pressure-sensitive adhesive dissolved in ethyl acetate. A release sheet was coated with the solution, followed by removal of the solvent ethyl acetate by drying. The laminate and a PET film backing layer were bonded together to obtain a nail patch of Example 5.

TABLE 4

| | |
|---|---|
| Terbinafine hydrochloride | 2.50% |
| Acrylic pressure-sensitive adhesive (DURO-TAK 87-2516, National Starch And Chemical Company) | 85.40% |
| Isopropyl myristate | 8.50% |
| Sodium acetate | 0.60% |
| Sorbitan monolaurate | 3.00% |
| Total | 100.00% |

Example 6

A nail patch of Example 6 was obtained in the same way as in Example 5 except that 5.0% terbinafine hydrochloride, 82.5% acrylic pressure-sensitive adhesive, 8.2% isopropyl myristate, and 1.3% sodium acetate were used.

Example 7

A nail patch of Example 7 was obtained in the same way as in Example 5 except that 7.5% terbinafine hydrochloride, 79.6% acrylic pressure-sensitive adhesive, 8.0% isopropyl myristate, and 1.9% sodium acetate were used.

Example 8

A nail patch of Example 8 was obtained in the same way as in Example 5 except that 10.0% terbinafine hydrochloride, 76.8% acrylic pressure-sensitive adhesive, 7.7% isopropyl myristate, and 2.5% sodium acetate were used.

Example 9

A nail patch comprising the composition shown in Table 5 below was produced. Specifically, terbinafine hydrochloride, sodium acetate, and sorbitan monolaurate were placed in a mortar in advance and well mixed. Then, this mixture was mixed with an acrylic pressure-sensitive adhesive dissolved in ethyl acetate. A release sheet was coated with the solution, followed by removal of the solvent ethyl acetate by drying. The laminate and a PET film backing layer were bonded together to obtain a nail patch of Example 9.

TABLE 5

| | |
|---|---|
| Terbinafine hydrochloride | 5.00% |
| Acrylic pressure-sensitive adhesive (DURO-TAK 87-2516, National Starch And Chemical Company) | 90.70% |
| Sodium acetate | 1.30% |
| Sorbitan monolaurate | 3.00% |
| Total | 100.00% |

Example 10

A nail patch comprising the composition shown in Table 6 below was produced. Specifically, terbinafine hydrochloride, sodium acetate, sorbitan monolaurate, and isopropyl myristate were placed in a mortar in advance and well mixed. Then, this mixture was mixed with an acrylic pressure-sensitive adhesive dissolved in ethyl acetate. A release sheet was coated with the solution, followed by removal of the solvent ethyl acetate by drying. The laminate and a PET film backing layer were bonded together to obtain a nail patch of Example 10.

TABLE 6

| | |
|---|---|
| Terbinafine hydrochloride | 5.00% |
| Acrylic pressure-sensitive adhesive (DURO-TAK 87-2516, National Starch And Chemical Company) | 88.50% |
| Isopropyl myristate | 2.20% |
| Sodium acetate | 1.30% |
| Sorbitan monolaurate | 3.00% |
| Total | 100.00% |

Example 11

A nail patch of Example 11 was obtained in the same way as in Example 10 except that 86.4% acrylic pressure-sensitive adhesive and 4.3% isopropyl myristate were used.

Example 12

A nail patch of Example 12 was obtained in the same way as in Example 10 except that 84.4% acrylic pressure-sensitive adhesive and 6.3% isopropyl myristate were used.

Example 13

A nail patch comprising the composition shown in Table 7 below was produced. Specifically, terbinafine hydrochloride, sodium acetate, and sorbitan monolaurate were placed in a mortar in advance and well mixed. Then, this mixture was mixed with an acrylic pressure-sensitive adhesive dissolved in ethyl acetate. A release sheet was coated with the solution, followed by removal of the solvent ethyl acetate by drying. The laminate and a PET film backing layer were bonded together to obtain a nail patch of Example 13.

TABLE 7

| | |
|---|---|
| Terbinafine hydrochloride | 10.00% |
| Acrylic pressure-sensitive adhesive (DURO-TAK 87-2194, National Starch And Chemical Company) | 82.00% |
| Sodium acetate | 5.00% |
| Sorbitan monolaurate | 3.00% |
| Total | 100.00% |

Example 14

A nail patch of Example 14 was obtained in the same way as in Example 13 except that 15.0% terbinafine hydrochloride, 74.5% acrylic pressure-sensitive adhesive, and 7.5% sodium acetate were used.

Example 15

A nail patch of Example 15 was obtained in the same way as in Example 13 except that 20.0% terbinafine hydrochloride, 67.0% acrylic pressure-sensitive adhesive, and 10.0% sodium acetate were used.

Example 16

A nail patch of Example 16 was obtained in the same way as in Example 13 except that 25.0% terbinafine hydrochloride, 59.5% acrylic pressure-sensitive adhesive, and 12.5% sodium acetate were used.

Example 17

A nail patch of Example 17 was obtained in the same way as in Example 13 except that 30.0% terbinafine hydrochloride, 52.0% acrylic pressure-sensitive adhesive, and 15.0% sodium acetate were used.

Example 18

Performance Evaluation on Nail Patches

<Release Test>

The nail patches obtained in Examples 1 to 17 and Comparative Example 1 were subjected to a release test using a dissolution tester NTR-6100 manufactured by Toyama Sangyo Co., Ltd. First, each of the nail patches was cut into a predetermined area, and this test piece was placed in a rotary cylinder after release of the release sheet. Next, hot water at 37° C. was circulated around the outer periphery of the cylinder. A polyethylene glycol-containing phosphate-buffered saline was used in the receptor layer. Sampling was conducted every two hours for 8 hours. A drug concentration in the obtained receptor solution was measured by high-performance liquid chromatography, and the amount of the drug released was calculated.

<Nail Device Test>

The nail patches obtained in Examples 1 to 17 and Comparative Example 1 were subjected to a nail device test. First, a normal human nail was cut into square pieces of a few mm per side, and this piece was caulked all about using silicon sheets and silicon bonds. The upper and lower parts of the caulked nail were held in silicon o-rings, which were in turn inserted in the main body of a device processed from a cryotube. Then, the tube was filled with a bovine serum albumin-containing phosphate-buffered saline (receiver solution). Next, each of the nail patches obtained in Examples 1 to 17 and Comparative Example 1 was attached to the upper surface of the nail and left at 32° C. for 3.5 days×2 pieces or for 5 days×1 piece. The nail piece was taken out thereof and dried. Then, the upper and intermediate layers of the nail were removed by polishing using a grinder to separate only the lower layer therefrom. The microconidia of *Trichophyton mentagrophytes* were inoculated to the undersurface of the nail piece and cultured at 35° C. for 7 days. Bacterial growth was visually observed, and the nail patches were separately assessed by scoring (drug efficacy score) based on the degree of growth on a scale of 0 to 4 (the bigger number represents the higher degree of growth). Then, the nail piece was dissolved by the addition of a 5 N aqueous NaOH solution. The amount of the drug extracted was measured by LC/MS/MS, and the amount of the drug in the nail was calculated. Moreover, the amount of the drug in the receiver solution was measured by LC/MS/MS, and the amount of the drug permeated into the nail was calculated.

<Hairless Mouse Skin Permeation Test>

The dorsal skin of a hairless mouse was abraded and placed in a flow-through-cell (5 cm$^2$) with the dermis positioned on the receptor layer side, while hot water at 37° C. was circulated around the outer periphery of the cell. Each of the nail patches obtained in Examples 1 to 4 and Comparative Example 1 was attached to the stratum corneum side. A saline was used in the receptor layer. Sampling was conducted every two hours for 24 hours at a rate of 5 mL/hour. The flow rate of the receptor solution obtained each time was accurately measured, and a drug concentration therein was measured by high-performance liquid chromatography. A permeability rate per hour was calculated from the measurement values of the flow rate and the drug concentration, and the amount of the drug permeated into the skin was determined.

<Performance Evaluation on Nail Patches of Examples 1 and 2>

The patches (Examples 1 and 2) comprising pressure-sensitive adhesive bases differing in the type of the acrylic pressure-sensitive adhesive were evaluated for the difference of performance. The evaluation results are shown in Table 8. From Table 8, it was confirmed that these acrylic pressure-sensitive adhesives offered almost no permeability into the skin, in spite of the large amount of terbinafine hydrochloride released, high permeability into the nail, and high antifungal effects. It was also confirmed that DURO-TAK 87-2516 exhibited higher permeability into the nail than that of the DURO-TAK 87-2194.

TABLE 8

| | Release test Amount of drug released (µg/cm$^2$) | Nail device test* | | | Skin permeation test Amount of drug permeated into skin (µg/cm$^2$) |
|---|---|---|---|---|---|
| | | Amount of drug in nail (ng) | Amount of drug permeated into nail (ng) | Drug efficacy score | |
| Example 1 | 12.0 | 0.7 | 0.3 | 2.3 | 0.0 |
| Example 2 | 14.6 | 1.3 | 1.0 | 1.3 | 0.0 |

*Test conditions: Two pieces of the preparation were used and attached to the nail for 1 week in total (3.5 days per piece).

<Performance Evaluation on Nail Patches of Examples 3 and 4 and Comparative Example 1>

The nail patches (Examples 3 and 4 and Comparative Example 1) comprising or not comprising the solubilizers or differing in the type of the added solubilizer were evaluated for the difference of performance. Specifically, the patch of Example 3 comprises sodium acetate and sorbitan monolaurate as solubilizers. The patch of Example 4 comprises sodium acetate and Tween 80 (instead of sorbitan monolaurate) as solubilizers. The patch of Comparative Example does not comprise the solubilizers. The evaluation results are shown in Table 9. From Table 9, it was confirmed that the sodium acetate largely contributes to permeability into the nail and that the sorbitan monolaurate also increases permeability into the nail.

TABLE 9

| | Release test Amount of drug released (µg/cm$^2$) | Nail device test* | | | Skin permeation test Amount of drug permeated into skin (µg/cm$^2$) |
|---|---|---|---|---|---|
| | | Amount of drug in nail (ng) | Amount of drug permeated into nail (ng) | Drug efficacy score | |
| Example 3 | 15.7 | 1.7 | 1.0 | 0.0 | 0.0 |
| Example 4 | 13.4 | 1.2 | 1.3 | 0.8 | 0.0 |
| Comparative Example 1 | 4.6 | 0.0 | 0.0 | 4.0 | 0.0 |

*Test conditions: Two pieces of the preparation were used and attached to the nail for 1 week in total (3.5 days per piece).

<Performance Evaluation on Nail Patches of Examples 5 to 8>

The nail patches (Examples 5 to 8) differing in the content of terbinafine hydrochloride were evaluated for the difference of performance. The evaluation results are shown in Table 10. From Table 10, it was confirmed that the amount of the drug released or permeability into the nail is increased with increases in the concentration of terbinafine hydrochloride and that antifungal effects also get higher with such increases.

TABLE 10

| | Release test Amount of drug released (µg/cm$^2$) | Nail device test* | | |
|---|---|---|---|---|
| | | Amount of drug in nail (ng) | Amount of drug permeated into nail (ng) | Drug efficacy score |
| Example 5 | 8.3 | 1.7 | 0.0 | 3.8 |
| Example 6 | 18.4 | 2.1 | 0.2 | 3.5 |

TABLE 10-continued

|  | Release test | Nail device test* | | |
| --- | --- | --- | --- | --- |
|  | Amount of drug released (μg/cm²) | Amount of drug in nail (ng) | Amount of drug permeated into nail (ng) | Drug efficacy score |
| Example 7 | 22.2 | 3.7 | 0.4 | 1.7 |
| Example 8 | 26.1 | 5.3 | 0.6 | 0.7 |

*Test conditions: One piece of the preparation was used and attached to the nail for 5 days.

<Performance Evaluation on Nail Patches of Examples 9 to 12>

The nail patches (Examples 9 to 12) comprising or not comprising the plasticizer isopropyl myristate or differing in the amount of the added plasticizer were evaluated for the difference of performance. The evaluation results are shown in Table 11. From Table 11, it was confirmed that the isopropyl myristate, even when not added or added at varying concentrations, hardly influenced permeability into the nail.

TABLE 11

|  | Release test | Nail device test* | | |
| --- | --- | --- | --- | --- |
|  | Amount of drug released (μg/cm²) | Amount of drug in nail (ng) | Amount of drug permeated into nail (ng) | Drug efficacy score |
| Example 9 | 16.9 | 1.2 | 0.7 | 3.3 |
| Example 10 | 13.9 | 1.5 | 0.3 | 3.3 |
| Example 11 | 15.4 | 0.9 | 0.4 | 3.0 |
| Example 12 | 15.1 | 0.9 | 0.4 | 3.5 |

*Test conditions: One piece of the preparation was used and attached to the nail for 5 days.

<Performance Evaluation on Nail Patches of Examples 13 to 17>

The nail patches (Examples 13 to 17) differing in the content of terbinafine hydrochloride were evaluated for the difference of performance. The evaluation results are shown in Table 12. From Table 12, it was confirmed that the amount of the drug released or permeability into the nail is increased with increases in the concentration of terbinafine hydrochloride and that antifungal effects also get higher with such increases.

TABLE 12

|  | Release test | Nail device test* | | |
| --- | --- | --- | --- | --- |
|  | Amount of drug released (μg/cm²) | Amount of drug in nail (ng) | Amount of drug permeated into nail (ng) | Drug efficacy score |
| Example 13 | 38.5 | 3.3 | 1.0 | 2.2 |
| Example 14 | 60.2 | 11.0 | 1.2 | 1.8 |

TABLE 12-continued

|  | Release test | Nail device test* | | |
| --- | --- | --- | --- | --- |
|  | Amount of drug released (μg/cm²) | Amount of drug in nail (ng) | Amount of drug permeated into nail (ng) | Drug efficacy score |
| Example 15 | 72.9 | 16.2 | 2.3 | 0.0 |
| Example 16 | 73.6 | 18.9 | 3.1 | 0.0 |
| Example 17 | 88.0 | 54.3 | 7.1 | 0.0 |

*Test conditions: One piece of the preparation was used and attached to the nail for 5 days.

The invention claimed is:

1. A nail patch comprising:
   a backing layer; and
   a pressure-sensitive adhesive layer disposed on at least one side of the backing layer, wherein the pressure-sensitive adhesive layer comprises:
   a pressure-sensitive adhesive base comprising an acrylic pressure-sensitive adhesive,
   terbinafine and/or a pharmacologically acceptable salt thereof present in an amount of from 5 to 50% by mass based on total mass of the pressure-sensitive adhesive layer, and
   a solubilizer comprising sodium acetate and sorbitan monolaurate.

2. The nail patch according to claim 1, wherein the acrylic pressure-sensitive adhesive is an acrylic copolymer having a hydroxyl or carboxylic acid group.

3. The nail patch according to claim 1, wherein the pressure-sensitive adhesive layer comprises 5 to 30% by mass of terbinafine and/or a pharmacologically acceptable salt thereof based on total mass of the pressure-sensitive adhesive layer.

4. The nail patch according to claim 1, wherein the pharmacologically acceptable salt of terbinafine is terbinafine hydrochloride.

5. The nail patch according to claim 1, wherein the pressure-sensitive adhesive layer further comprises a plasticizer.

6. A nail patch comprising:
   a backing layer; and
   a pressure-sensitive adhesive layer disposed on at least one side of the backing layer, wherein the pressure-sensitive adhesive layer comprises:
   a pressure-sensitive adhesive base comprising an acrylic pressure-sensitive adhesive,
   terbinafine and/or a pharmacologically acceptable salt thereof present in an amount of from 5 to 50% by mass based on total mass of the pressure-sensitive adhesive layer, and
   a solubilizer consisting of sodium acetate and sorbitan monolaurate.

* * * * *